United States Patent [19]

Piper et al.

[11] Patent Number: 5,077,404

[45] Date of Patent: Dec. 31, 1991

[54] CYCLIZED 5,10-DIDEAZAAMINOPTERIN COMPOUNDS

[76] Inventors: James R. Piper, 3128 Dolly Ridge Dr., Birmingham, Ala. 36234; John A. Montgomery, 3596 Springhill Rd., Birmingham, Ala. 35223; Francis M. Sirotnak, 80 East End Ave., New York, N.Y. 10128; Joseph I. DeGraw, 880 Hanover Ave., Sunnyvale, Calif. 94087

[21] Appl. No.: 399,840

[22] Filed: Aug. 29, 1989

[51] Int. Cl.$^5$ .......................................... C07D 239/70
[52] U.S. Cl. .................................. 544/250; 544/299
[58] Field of Search ................ 544/234, 250; 514/258, 514/267

[56] References Cited

U.S. PATENT DOCUMENTS

| | | | |
|---|---|---|---|
| 4,460,591 | 7/1984 | DeGraw et al. | 544/279 |
| 4,684,653 | 8/1987 | Taylor et al. | 514/258 |

OTHER PUBLICATIONS

*Synthesis of the Antileukemic Agents* . . . , Taylor et al., J. Med. Chem., 28, 914–921 (1985).
*Synthesis of 5,10–Dideazaaminopterin* . . . , DeGraw et al., J. Heterocyclic Chem., 23, 1–4 (1986).
*Synthesis and Antifolate Activity* . . . , Piper et al., J. Med. Chem., 31, 2164–2169.

*Primary Examiner*—Mukund J. Shah
*Assistant Examiner*—Jyothsna Venkat
*Attorney, Agent, or Firm*—Roylance, Abrams, Berdo & Goodman

[57] ABSTRACT

5,10-Dialkyl substituted 5,10-dideazaaminopterins and a cyclized derivative thereof are disclosed as potent antineoplastic agents. Also disclosed is an improved process for the preparation of 10-ethyl-10-deazaaminopterin using the intermediate methyl 4-[[2-(2,4-diamino-6-pteridinyl)-1-ethyl]ethenyl]benzoate.

2 Claims, No Drawings

CYCLIZED 5,10-DIDEAZAAMINOPTERIN COMPOUNDS

REFERENCE TO GOVERNMENT GRANT

The invention described herein was made in the course of work under a grant from the National Institute of Health.

BACKGROUND OF THE INVENTION

This invention relates to 5,10-dialkyl substituted 5,10-dideazaaminopterin and a cyclized derivative thereof and to the use of such compounds as antineoplastic agents. Another aspect of this invention relates to an improved process for the preparation of 10-ethyl-10-deazaaminopterin.

Methotrexate (MTX) remains the only classical antifolate in established clinical use, and its use has continued to expand as new methods of administering the drug have been introduced and as other tumor types have been added to the list of those now being treated. MTX usage, however, suffers major limitations due to its toxic side effects and the development of resistance by tumor cells. Some tumors are naturally resistant to MTX while others acquire resistance after a period of response. Three factors known to contribute to drug resistance are (a) loss of the active-transport system by which MTX enters cells, (b) increased levels of dihydrofolate reductase (DHFR) the intracellular target of MTX, and (c) the presence of structurally altered DHFR having lower affinity for MTX. Another explanation of resistance may be offered in the recent description of a structurally altered DHFR from an MTX-resistant mutant cell line with unaltered affinity for MTX, but with greater capacity to reduce dihydrofolate than the DHFR from the parent MTX-sensitive cell line. MTX and aminopterin (AMT) have the following structures:

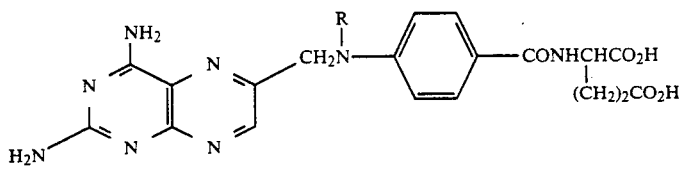

AMT: R = H
MTX: R = CH₃

As part of program aimed toward the identification of new antifolate agents that exert greater therapeutic effectiveness against a broader spectrum of tumors than agents now available, antifolates are sought having favorably altered transport characteristics but still possessing tight binding affinity for DHFR. In studies aimed toward greater understanding of transport properties, differences have been observed between tumor and normal proliferative tissue in mediated cellular membrane transport of antifolates and in the intracellular γ-polyglutamylation of the agents. These biochemical parameters appear to be critical determinants for selective antitumor activity. In studies that document these differences, positions 5 and 10 on the classical antifolate-type molecular structure have been identified as sites where modification does not reduce binding to DHFR but does influence transport efficacy to favor inward flux into tumor cells and also intracellular γ-polyglutamylation resulting in greater accumulation in tumor cells than in normal cells.

The above findings were exploited in the design of the 10-deazaaminopterin series of antifolates (DeGraw et al, J. Med. Chem., 17, 552 [1974]; DeGraw and Sirotnak, U.S. Pat. No. 4,393,964). This series, particularly 10-ethyl-10-deazaaminopterin (reviewed in DeGraw et al, J. Med. Chem., 29, 1056 [1986]), exhibited markedly enhanced therapeutic selectivity compared to MTX in both animal solid tumor models and human tumor xenografts (Schmid et al, Cancer Treat. Rep; 69, 551 [1985]). In on-going clinical trials, 10-ethyl-10-deazaaminopterin has shown significant therapeutic activity against non-small cell lung cancer (Shum et al, J. Clin. Oncol., 6, 446 [1988]; Kris et al, Proc. of ASCO, San Francisco, May 21-23, 1989; Abstr No. 884).

Current studies with the 5-deaza analogues of AMT and MTX (Piper et al, J. Med. Chem., 29, 1080 [1986] and U.S. Pat. No. 4,725,687) have revealed that 5-alkyl-5-deaza analogues of AMT and MTX are more active in vivo than MTX against four murine tumor models (Sirotnak et al, Cancer Res., 48, 5686 [1988]).

5,10-Dideazaaminopterin is disclosed by Taylor et al in J. Med. Chem., 28, 914-921 (1985) and by DeGraw et al in J. Heterocyclic Chem., 23, 1-4 (1986). 5-Methyl-5,10-dideazaaminopterin is disclosed by Piper et al in J. Med. Chem., 31, 2164-2169 (1988). Neither 5,10-dideazaaminopterin nor 5-methyl-5,10-dideazaaminopterin showed evidence of biological activity significantly greater than that of MTX.

U.S Pat. No. 4,684,653 to Taylor et al discloses compounds having the formula where R is defined as hydrogen, methyl or ethyl as antineoplastic agents.

SUMMARY OF THE INVENTION

It has now been discovered that 5,10-dialkyl substituted 5,10-dideazaaminopterin and a cyclized derivative thereof are especially valuable antineoplastic agents. These compounds have the structures:

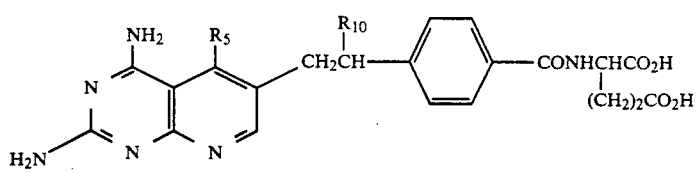

I

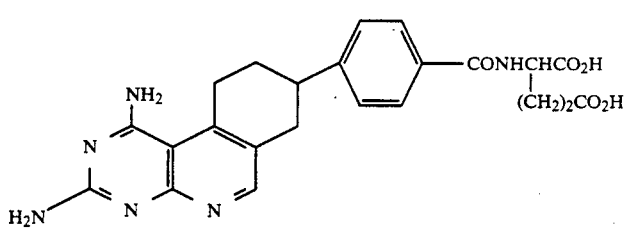

II wherein $R_5$ and $R_{10}$ represent alkyl groups containing from 1-6 carbon atoms. It will be appreciated that Structure II is similar to Structure I in that $R_5$ and $R_{10}$ taken together represent an ethylene ($-CH_2CH_2-$) group.

An improved process for the production of 10-ethyl-10-deazaaminopterin has also been discovered which involves the production and use of the intermediate methyl 4-[[2-(2, 4-diamino-6-pteridinyl)-1-ethyl]ethenyl]-benzoate.

DETAILED DESCRIPTION OF THE INVENTION

In the description which follows, reference will be made to Arabic numbers which identify compounds shown by structural formulas in Schemes I and II. Scheme I is as follows:

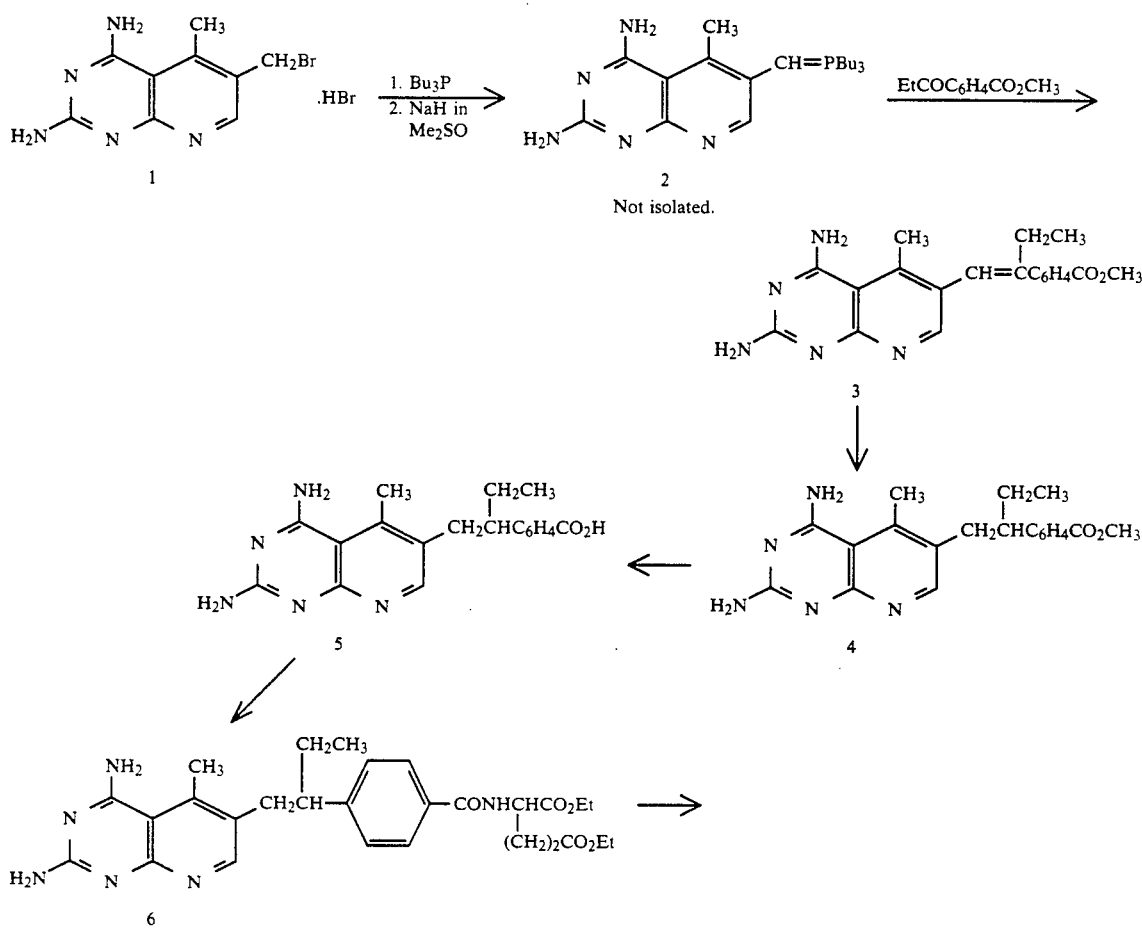

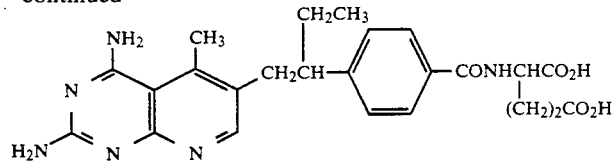

7

Synthesis of 10-ethyl-5-methyl-5,10-dideazaaminopterin (7 in Scheme I above which corresponds to general Structure I where $R_5=CH_3$ and $R_{10}=CH_2CH_3$) was achieved as shown below beginning with 6-(bromomethyl)-2,4-diamino-5-methyl-pyrido[2,3-d]pyrimidine hydrobromide (1). (The bromomethyl compound 1 was described by Piper et al in J. Med Chem., 29, 1080 (1986) and in U.S. Pat. No. 4,725,687). The bromomethyl compound 1 was treated with tributylphosphine ($Bu_3P$) in dimethyl sulfoxide ($Me_2SO$), and the resulting tributylphosphonium salt was treated in situ with sodium hydride to give the ylide intermediate 2 which remained in solution in $Me_2SO$. Methyl 4-(propionyl)-benzoate was then added to the solution, and the desired Wittig reaction to produce the olefinic intermediate 3 occurred as expected. The product 3 was isolated and purified by column chromatography on silica gel. Hydrogenation of the olefinic bridge of 3 followed. This step was achieved in glacial acetic acid promoted by palladium-on-carbon (Pd/C) catalyst under hydrogen at ambient conditions in a gas burette. The desired hydrogenated product 4 was separated from unwanted coproducts and unchanged 3 by silica gel chromatography. Saponification of the ester group of 4 in $Me_2SO$ containing a slight excess of aqueous sodium hydroxide followed. Following removal of the $Me_2SO$, the product 5 was isolated by acidification of an aqueous solution of its sodium salt. Coupling of 5 with diethyl L-glutamate followed; the reaction was promoted by diethyl cyanophosphonate in $Me_2SO$ containing N-methylmorpholine. The coupled product 6 was purified by chromatography on silica gel. Saponification of the ester groups of 6 was carried out at room temperature in aqueous methanol containing a small excess of sodium hydroxide to give the disodium salt of the target compound, and acidification of the solution caused precipitation of target compound 10-ethyl-5-methyl-5,10-dideazaaminopterin (7).

The synthetic route used to prepare 7 is similar in principle to one described for synthesizing 10-deazaaminopterin (Piper and Montgomery, J. Med. Chem., 23, 320 [1980] and U.S. Pat. No. 4,172,200). Three important differences in the syntheses are: first, the route to 10-deazaaminopterin made use of a triphenylphorphorane intermediate for a Wittig reaction with an aldehyde co-reactant in N,N-dimethylacetamide, whereas the present method required the less sterically bulky tributylphosphorane for Wittig reaction with a keto co-reactant and required $Me_2SO$ as solvent. Second, the key Wittig reaction, which afforded intermediate 3, gave better results using methyl 4-(propionyl)benzoate than when diethyl N-[(4-propionyl)-benzoyl]-L-glutamate was used, whereas in the earlier synthesis of 10-deazaaminopterin, the use of the complete glutamate-bearing side chain proved satisfactory. Thus, the glutamic acid moiety had to be introduced after the Wittig conversion in the synthesis of 7. The third difference is that in the hydrogenation step during synthesis of 10-deazaaminopterin, platinum catalyst is used as the catalyst. This catalyst promotes hydrogenation, not only of the olefinic bridge, but also the pyrazine-ring moiety affording a tetrahydro derivative of the intended product; however, the aromaticity of the pyrazine-ring moiety is easily regenerated by mild oxidation with aqueous hydrogen peroxide. In the 5-deaza analogue, however, reversal of hydrogenation of the pyrido-ring moiety could not be done easily, if at all. It is therefore important to avoid hydrogenation other than in the olefinic bridge. For this reason, in the hydrogenation of the olefin precursor to 7, conditions were selected to try to minimize hydrogenation within its pyrido-ring moiety.

In working out the conditions that made the key Wittig condensation with methyl 4-(propionyl)benzoate effective, use was made of available 6-(bromomethyl)-2,4-pteridinediamine hydrobromide (Piper and Montgomery, J. Org. Chem., 42, 208 [1977] and in U.S. Pat. Nos. 4,077,957 and 4,079,056) as a model or prototype for 6-(bromomethyl)-2 4-diamino-5-methylpyrido[2,3-d]pyrimidine hydrobromide (1). The full-pteridine analogue was used in the experiments that led to the findings that $Me_2SO$ was the clear solvent of choice and that tributylphosphine would allow the Wittig conversion to occur, whereas triphenylphosphine would not. The conversion shown below to produce methyl 4-[[2-(2,4-diamino-6-pteridinyl)-1-ethyl]ethenyl]benzoate (10) then served as a guide model for the preparation of the 5-methyl-5-deaza analogue 3. Very similar results were obtained from both conversions.

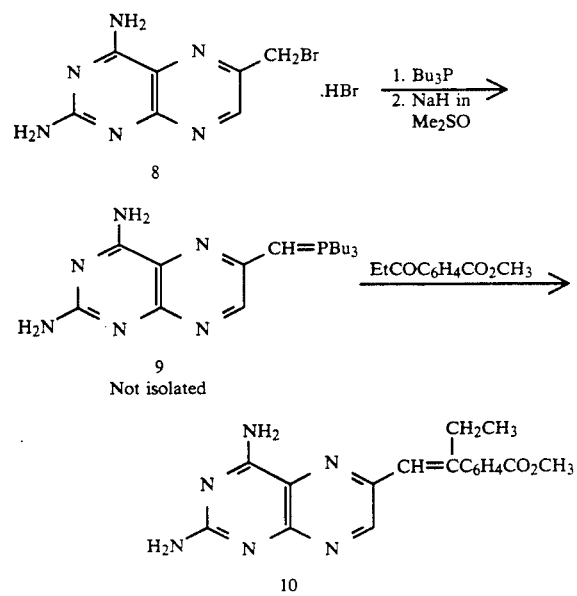

Compound 10 may then be converted to 10-ethyl-10-deazaaminopterin in the manner previously described for the conversion of Compound 3 to 5-methyl-10-ethyl-5,10-dideazaaminopterin, Compound 7. Thus, another aspect of this invention comprises a process for the preparation of 10-ethyl-10-deazaaminopterin by hydrogenating Compound 10, saponifying the ester group from said hydrogenated compound, coupling said saponified product with diethyl-1-glutamate, and saponifying the ester groups from the resultant product to yield 10-ethyl-10-deazaaminopterin.

The compound of Structure II, 5,10-ethano-5,10-dideazaaminopterin, may be prepared by the following scheme:

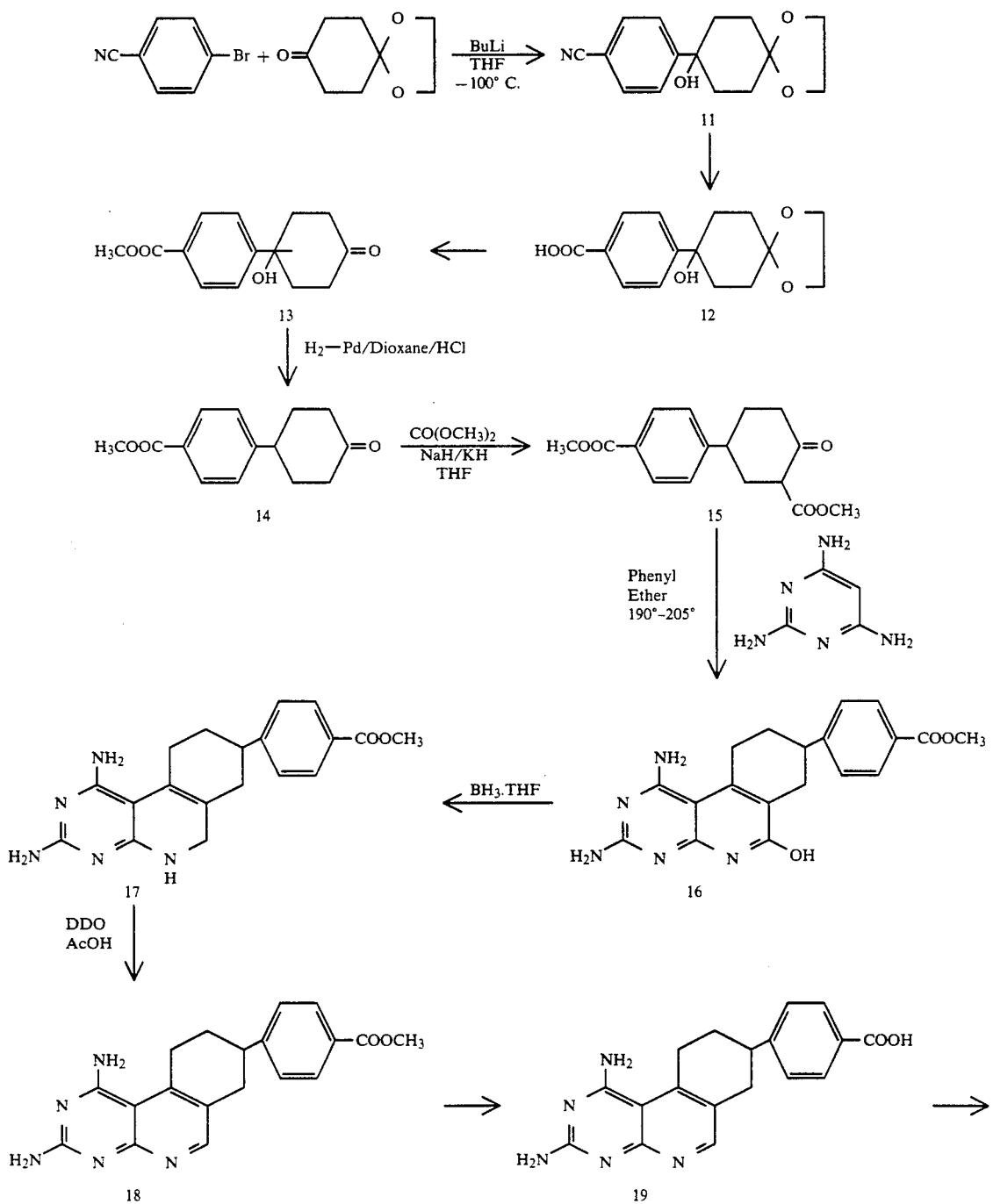

-continued
Scheme II

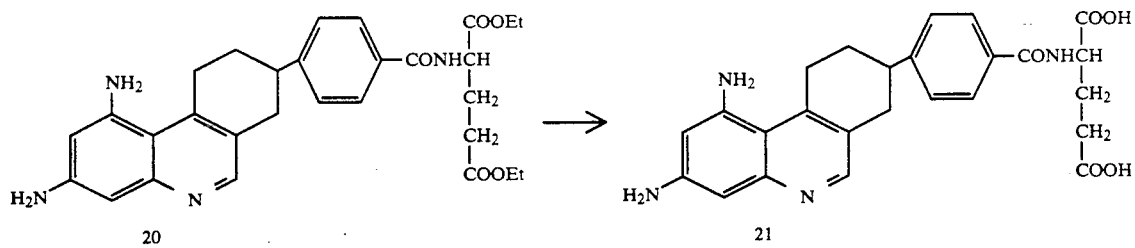

The compounds of this invention form pharmaceutically acceptable salts with both organic and inorganic acids. Examples of suitable acids for salt formation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with an equivalent amount of the desired acid in the conventional manner. The free base form may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base form differs from its respective salt forms somewhat in certain physical properties such as solubility in polar solvents, but the salts are otherwise equivalent to the respective free base form for purposes of this invention.

The compounds of this invention also form pharmaceutically acceptable carboxylate salts by reacting a suitable base with one or more of the free carboxyl groups. Suitable bases include alkali metal or alkaline earth metal hydroxides or carbonates, for example, sodium hydroxide, potassium hydroxide, calcium hydroxide, magnesium hydroxide, and corresponding carbonates; and nitrogen bases such as ammonia and alkylamines such as trimethylamine and triethylamine.

The novel compounds of the present invention inhibit transplanted mouse tumor growth when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 grams of the active compounds for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry- or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compounds as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

The following examples illustrate the best mode known for carrying out this invention. In these examples, examinations by TLC were performed on Analtech precoated (250-$\mu$M)silica gel G(F) plates. Products were dried in vacuo (1 mm or less) at 22°-25° C. over $P_2O_5$ and NaOH pellets. Final products were dried and then allowed to equilibrate under ambient conditions. Mass spectra were recorded on a Varian MAT 11A mass spectrometer in the fast-atom-bombardment mode. UV spectra were determined with a Perkin-Elmer Model Lambda 9 spectrometer. Samples were first dissolved in 0.1N NaOH, and the solutions were diluted 10-fold with the medium given in the listing. Maximma are expressed in nanometers with molar absorbance given in parentheses. Molecular weights used in calculations conform with the compositions listed with the elemental analysis results. The following abbreviations are used in the examples: $Me_2SO$ is dimethylsulfoxide, $Et_2O$ is ethylether, AcOH is acetic acid, MeOH is methyl alcohol and THF is tetrahydrofuran.

EXAMPLE 1

Methyl 4-[[2-(2,4-Diamino-5-methylpyrido[2,3-d]-pyrimidin-6-yl)-1-ethyl]ethenyl]benzoate (3). A solution of the bromomethyl compound 1 (3.13 g, 8.24 mmol) and tributylphosphine (5.00 g, 24.7 mmol) in $Me_2SO$ (200 mL) was kept 20 hours at 20°-23° C., then gradually warmed during 90 minutes to 55° C. for 30 minutes, and cooled to 20-23° C. Methyl 4-(propionyl)benzoate (1.58 g. 8.22 mmol) was then added, followed by sodium hydride (660 mg of 60% dispersion in oil, 16.5 mmol). Complete solution occurred readily. After 44 hours at 20°-23° C., the solution was heated at 70°-75° C. for 64 hours. Removal of the $Me_2SO$ by distillation in vacuo (less than 1 mm, bath to 55° C.) followed. The syrupy residue was stirred with $Et_2O$ until the yellow solid that formed was dispersed. The solid was collected with the aid of $Et_2O$, air dried, then stirred thoroughly with $H_2O$ before it was again collected and dried in vacuo (78° C.) over NaOH pellets and $P_2O_5$) Crude 3 (2.31 g, 77% crude yield) was combined with a sample from another run and the combined batch was purified by flash chromatography on silica gel (230–400 mesh) using elution by $CHCl_3$-MeOH (9:1). Fractions found by TLC to be homogeneous (UV detection) were pooled and evaporated to give pure 3. The purified material amounted to 50% recovery of material applied to the column. Spectral data: mass, m/z 364, (MH+) for $C_{20}H_{21}N_5O_2$.

EXAMPLE 2

Methyl 4-[1-[(2,4-Diamino-5-methylpyrido[2,3-d]-pyrimidin-6-yl)methyl]propyl]benzoate (4). Compound 3 (710 mg, 2.51 mmol) in glacial AcOH was treated with stirring with 30% Pd/C (120 mg) for 10 minutes, then 5% Pd/C (1.40 g) was added. Hydrogenation at atmospheric pressure (gas burette) followed. After 2 hours, uptake of hydrogen had reached 100 mL and the rate had slowed from a peak rate of 1 mL per minute to about 1 mL per 8 minutes. Examination at this point by TLC indicated two unwanted coproducts formed by hydrogenation in the pyrido ring moiety. Hydrogenation was discontinued, and workup was begun. The catalyst was removed by filtration and extracted on the funnel by stirring with methanol. The methanol washings of the catalyst were combined with the original acetic acid filtrate. The MeOH-AcOH solution was then combined with that from another run with similar experiences (on 360 mg of with an uptake of 53 mL of hydrogen). The clear pale-yellow solution was evaporated under reduced pressure (H₂O aspirator, rotary evaporator, bath to 55° C.) until nearly all the AcOH had been removed. The concentrated yellow oil that remained was treated with Et20 to cause separation of crude 4 as a beige solid. The mixture was stirred until the solid was well dispersed before it was collected. Examination by TLC (CHCl$_3$-MeOH, 4:1) of the Et$_2$O-insoluble solid and the ethereal filtrate revealed the solid to be considerably less contaminated by two faster-moving coproducts (from ring reduction) and unchanged starting material (spot barely above that due to desired product) than the ethereal filtrate. The solid (670 mg, 66% crude yield) required further purification. (Unchanged 3 proved more difficult to remove than the excessively hydrogenated coproducts. This experience suggests that some degree of ring hydrogenation during the preparation of 4 would be acceptable provided conversion of starting 3 is complete) The ethereal filtrate was evaporated, and the residual viscous yellow oil was stirred with H$_2$O and treated with saturated NaHCO$_3$ solution to produce pH 8. The yellow solid which formed was collected, dried in vacuo, and examined by TLC. This portion of the product mixture consisted mostly of the two excessively hydrogenated coproducts plus some unchanged 3 and some 4. This crude fraction was applied in CHCl$_3$MeOH (1:1) solution to a preparative TLC plate which was developed using CHCl$_3$-MeOH (4:1) to give a band which consisted mostly of 4 plus some unconverted 3. Extraction of this band afforded 60 mg of material of about the same purity as the Et$_2$O-insoluble portion isolated earlier. The two portions (670 mg plus 60 mg) were combined for flash-column chromatography. Two column runs followed, the first using CHCl$_3$-MeOH (4:1) and the second using CHCl$_3$-MeOH (7:1). The column fractions which appeared essentially homogeneous in 4 according to TLC were combined and evaporated to give 370 mg (34%), but a sizeable portion of the desired product was left in unresolved fractions contaminated by unconverted 3. Spectral data for 4: mass, m/z 366, MH+ for C$_{20}$H$_{23}$N$_5$O$_2$.

EXAMPLE 3

4-[1-[(2,4-Diamino-5-methylpyrido[2,3-d]pyrimidin-6-yl)methyl]propyl]benzoic Acid (5). A solution of 4 (190 mg, 0.521 mmol) in Me$_2$SO (17 mL) was treated with 1 N NaOH (0.75 mL). After 20 hours at 20°-23° C., the solution was found by TLC (CHCl$_3$-MeOH, 4:1) examination to contain a small amount of unchanged 4. More 1N NaOH (0.50 mL) was added to the solution, kept at 20°-23° C., and 2 hours later TLC showed completed disappearance of 4. The Me$_2$SO was then removed by distillation in vacuo (less than 1 mm, bath to 45° C). The residue was dissolved in H$_2$O (3 mL), and the resulting clear solution was carefully treated dropwise with 1N HCl to produce pH 5 and cause precipitation of 5 as a pale-beige solid. The mixture was chilled in a refrigerator for several hours before the solid was collected and dried; yield 165 mg (82%). Anal. Calcd. for C$_{19}$H$_{21}$N$_5$O$_2$.2H$_2$O: C, 58.90; H, 6.50; N, 18.08. Found: C, 59.40; H, 6.14; N, 17.63. Spectral data: mass, m/z 352, MH+ for C$_{19}$H$_{21}$N$_5$O$_2$; UV λmax 234 nm (ε 39 300), 322 (7730) at pH 1; 235 nm (ε 37 800), 335 (6050) at pH 7; 236 nm (ε 37 600), 346 (6730) at pH 13.

EXAMPLE 4

Diethyl N-[4-[1-[(2,4-Diamino-5-methylpyrido[2,3-d]-pyrimidin-6-yl)methyl]propyl]benzoyl]-L-glutamate (6). A solution of 5.2H$_2$O (155 mg, 0.400 mmol) in Me$_2$SO (25 mL) was treated with N-methylmorpholine (124 mg of 98%, 1.20 mmol) and diethyl cyanophosphonate (206 mg of 95%, 1.20 mmol). The resulting solution was kept at 20°-23° C. for 62 hours. Me$_2$SO was removed by distillation in vacuo (bath to 45° C.), and the residue was treated with H$_2$O (5 mL). The resulting acidic solution was treated with 10% NaHCO$_3$ solution to produce pH 9 and cause precipitation of 6 as a beige solid. After a refrigeration period (2 hours), the solid was collected and dried. Crude 6 (192 mg) thus obtained was combined with a sample (60 mg) obtained from a smaller run for purification. Initially, the material was subjected to gravity flow chromatography on a short (4 cm × 10 cm) silica gel column (70-230 mesh) eluted with CHCl$_3$-MeOH (4:1). A fast-moving UV-absorbing contaminant was essentially removed before the desired 6 began eluting. Fractions nearly pure in 6 were combined and evaporated to give 160 mg of material. Further purification was necessary, however, and this was done on a preparative TLC plate developed with CHCl$_3$-MeOH (4:1) after application in MeOH solution. The band due to 6 was removed and extracted with MeOH. Evaporation of the filtered solution gave pure 6 (100 mg). Spectral data: mass, m/z 537, MH+ for C$_{28}$H$_{36}$N$_6$O$_5$.

EXAMPLE 5

N-[4-[1-[(2,4-Diamino-5-methylpyrido[2,3-d]pyrimidin-6-yl)methyl]propyl]benzoyl]-L-glutamic Acid (7) or 10-Ethyl-5-methyl-5,10-dideazaaminopterin. The extract from the excised plate band described under 6 above (100 mg) was dissolved in MeOH (15 mL) containing 1 N NaOH (0.5 mL), and the pale-yellow solution was kept at 20-23° C. for 20 hours MeOH was then removed under reduced pressure (H$_2$O aspirator, bath at 20°-25° C.), and the residue was dissolved in H$_2$O (6 mL). This solution was kept 24 hours at 20°-23° C. before it was filtered to insure clarity. The filtrate was then carefully treated dropwise with 1N HCl to produce pH 3.8 (meter) and precipitate 7 as a light-beige solid. The mixture was kept in an ice-H$_2$O bath for 1.5 hours before the solid was collected with the aid of cold H$_2$O and dried. After removal from the drying chamber, the sample was allowed to equilibrate with ambient conditions where it underwent a weight increase from 67 mg initially to 72 mg finally. This increase corresponds with that calculated for the transition of anhydrous 7 (Mol. Wt. 480.5) to its dihydrate (Mol. Wt. 516.6). The yield from 6 was 75%. Anal. Calcd. for C$_{24}$H$_{28}$N$_6$O$_5$.2H$_2$O; C, 55.80; H, 6.24; N, 16.27. Found: C, 55.88; 55.85; H, 5.95, 6.21; N, 16.32, 16 27. Spectral data: mass, m/z 481, MH+; UV λmax 233 nm (ε 40 600), 321 (7890) at pH 1; 235 nm (ε40 600), 334 (6100) at pH 7; 237 nm (ε 40 600), 346 (6820) at pH 13.

EXAMPLE 6

4-(4'-Cyanophenyl)-4-hydroxycyclohexanone ethylene ketal (11). 4-Bromobenzonitrile was treated in THF-hexane with n-butyllithium at −100° C. Cyclohexanedione monoethylene ketal was added at −100° to give 70% yield of 11.

EXAMPLE 7

4-(4'-Carbomethoxyphenyl)cyclohexanone (14). Compound 11 was heated in 2-methoxyethanol.2N NaOH at 100° to yield 12 (94%). Esterification and deprotection in refluxing MeOH containing HCl and a small amount of H$_2$O gave a quantitative recovery of 13. Hydrogenation of 13 in 1% concentrated HCl/dioxane in the presence of palladium black at 40°–48° afforded 14 in a 39% yield.

EXAMPLE 8

2-Carbomethoxy-4-(4'-carbomethoxyphenyl)cyclohexanone (15). Compound 14 was acylated with dimethylcarbonate/NaH/-KH in THF to give 15 (63%).

EXAMPLE 9

Methyl-4-amino-4-deoxy-5,10-ethano-5,10-dideazapteroate (18). Compound 15 was reacted with 2,4,6-triaminopyrimidine in phenyl ether at 190°–205° to give 16 in 82% yield. Compound 16 was treated with 1M borane. THF affording 17 (56% yield). Reaction of 17 with DDQ in acetic acid gave 18 in 61% yield.

EXAMPLE 10

5,10-Ethano-5,10-dideazaaminopterin diethyl ester (20). Compound 18 was hydrolyzed with NaOH in 2-methoxyethanol to give 19 (80% yield). Compound 19 was coupled with diethyl-L-glutamate.HCl affording 10 in 44% yield.

EXAMPLE 11

5,10-Ethano-5,10-dideazaaminopterin (21). The diester 20 was saponified with 1N NaOH in 2-methoxyethanol to give 21 in 73% yield.

What is claimed is:

1. A compound having the structure:

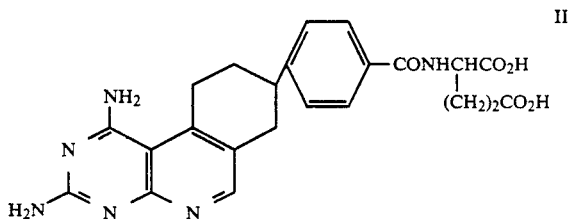

wherein R$_5$ and R$_{10}$ represent alkyl groups containing from 1-6 carbon atoms.

2. 5,10-Ethano-5,10-dideazaaminopterin.

* * * * *

UNITED STATES PATENT AND TRADEMARK OFFICE
CERTIFICATE OF CORRECTION

PATENT NO. : 5,077,404

DATED : December 31, 1991

INVENTOR(S) : James R. Piper, John A. Montgomery, Francis M. Sirotnak and Joseph I. DeGraw It is certified that error appears in the above-identified patent and that said Letters Patent is hereby corrected as shown below:

On the title page, following "Inventors:" should appear -- Assignees: James R. Piper and John A. Montgomery have assigned their interest to Southern Research Institute, Birmingham, Alabama, and Francis M. Sirotnak has assigned his interest to Sloan-Kettering Institute for Cancer Research, New York, New York. --

Col. 16, cancel claim 1.

Signed and Sealed this

Twenty-third Day of March, 1993

Attest:

STEPHEN G. KUNIN

*Attesting Officer*      Acting Commissioner of Patents and Trademarks